(12) United States Patent
Patterson et al.

(10) Patent No.: US 10,497,463 B2
(45) Date of Patent: Dec. 3, 2019

(54) AUTOMATED NUCLEIC ACID REPEAT COUNT CALLING METHODS

(71) Applicant: Myriad Women's Health, Inc., South San Francisco, CA (US)

(72) Inventors: A. Scott Patterson, South San Francisco, CA (US); Imran S. Haque, South San Francisco, CA (US); Eric A. Evans, South San Francisco, CA (US); Clement Chu, South San Francisco, CA (US)

(73) Assignee: MYRIAD WOMEN'S HEALTH, INC., South San Francisco, CA (US)

( * ) Notice: Subject to any disclaimer, the term of this patent is extended or adjusted under 35 U.S.C. 154(b) by 971 days.

(21) Appl. No.: 14/540,334

(22) Filed: Nov. 13, 2014

(65) Prior Publication Data

US 2015/0134267 A1    May 14, 2015

Related U.S. Application Data

(60) Provisional application No. 61/904,439, filed on Nov. 14, 2013, provisional application No. 61/903,847, filed on Nov. 13, 2013.

(51) Int. Cl.
*G16B 30/00* (2019.01)
*G16B 20/00* (2019.01)

(52) U.S. Cl.
CPC ............ *G16B 30/00* (2019.02); *G16B 20/00* (2019.02)

(58) Field of Classification Search
None
See application file for complete search history.

(56) References Cited

U.S. PATENT DOCUMENTS

| 5,502,773 | A  | 3/1996  | Tibbetts et al. |
| 7,855,053 | B2 | 12/2010 | Hagerman et al. |
| 8,409,805 | B2 | 4/2013  | Latham |
| 2010/0243451 | A1 | 9/2010 | Latham et al. |
| 2010/0261158 | A1 | 10/2010 | Nordman et al. |

OTHER PUBLICATIONS

Azimi, M. et al. (May 2016; e-published on Jan. 29, 2016). "Carrier Screening by Next-Generation Sequencing: Health Benefits and Cost Effectiveness," *Molecular Genetics & Genomic Medicine* 4(3):292-302.

(Continued)

*Primary Examiner* — Joseph Woitach
(74) *Attorney, Agent, or Firm* — FisherBroyles, LLP; Victoria Brewster; Gregory Fettig

(57) ABSTRACT

The present disclosure relates to processes for determining the number of nucleic acid repeats in a DNA fragment comprising a nucleic acid repeat region. One example method may include receiving DNA size and abundance data generated by resolving DNA amplification products. A set of low-pass data may be generated by applying a low-pass filter to the DNA size and abundance data and a set of band-pass data may be generated by applying a band-pass filter to the DNA size and abundance data. A peak of the DNA size and abundance data representative of a number of nucleic acid repeats in the DNA may be identified based on peaks identified from the low-pass data and the band-pass data.

32 Claims, 8 Drawing Sheets

(b) Filtered data and called peaks

(56) References Cited

OTHER PUBLICATIONS

Bailey, D.B. et al. (Aug. 2009; e-published on Jul. 5, 2009). "No Change in the Age of Diagnosis for Fragile X Syndrome: Findings From a National Parent Survey," *Pediatrics* 124(2):527-533.

Chen, L. et al. (Sep. 2010). "An Information-Rich CGG Repeat Primed PCR that Detects the Full Range of Fragile X Expanded Alleles and Minimizes the Need for Southern Blot Analysis," *Journal of Molecular Diagnostics* 12(5):589-600.

Christie, L. et al. (Feb. 2013; e-published on Jan. 9, 2013). "Maternal Attitudes to Newborn Screening for Fragile X Syndrome," *American Journal of Medical Genetics, Part A* 161A(2):301-311.

Coffee, B. et al. (Oct. 9, 2009). "Incidence of Fragile X Syndrome by Newborn Screening for Methylated FMR1 DNA," *The American Journal of Human Genetics* 85(4):503-514.

Eppstein, D. et al. (2007; e-published on Jan. 12, 2007). "Improved Combinatorial Group Testing Algorithms for Real-World Problem Sizes," *SIAM Journal on Computing* 36(5):1360-1375.

Erlich, Y. et al. (Feb. 2010). "Compressed Genotyping," *IEEE Trans Inf Theory* 56(2):706-723.

Erlich, Y. et al. (Jul. 2009; e-published on May 15, 2009). "DNA Sudoku—Harnessing High-Throughput Sequencing for Multiplexed Specimen Analysis," *Genome Research* 19(7):1243-1253.

Filipovic-Sadic, S. et al. (Mar. 2010; e-published on Jan. 7, 2010). "A Novel FMR1 PCR Method for the Routine Detection of Low Abundance Expanded Alleles and Full Mutations in Fragile X Syndrome," *Clinical Chemistry* 56(3):399-408.

Hantash, F.M. et al. (Mar. 2010; e-published on Feb. 17, 2010). "Qualitative Assessment of FMR1 (CGG)n. Triplet Repeat Status in Normal, Intermediate, Premutation, Full Mutation, and Mosaic Carriers in Both Sexes: Implications for Fragile X Syndrome Carrier and Newborn Screening," *Genetics in Medicine* 12(3):162-173.

Kainkaryam, R.M. (2010). "Pooling Designs for High-Throughput Biological Experiments," PhD thesis, The University of Michigan, one hundred and thirty five pages.

Loomis, E.W. et al. (Jan. 2013; e-published on Oct. 11, 2012). "Sequencing the Unsequenceable: Expanded CGG-repeat Alleles of the Fragile X Gene," *Genome Research* 23(1):121-128.

Margolis, R.L. (Oct. 2003). "Diagnosis of Huntington Disease," *Clinical Chemistry* 49(10):1726-1723.

Monaghan, K.G. et al. (Jul. 2013, e-published on Jun. 13, 2013). "ACMG Standards and Guidelines for Fragile X Testing: A Revision to the Disease-Specific Supplements to the Standards and Guidelines for Clinical Genetics Laboratories of the American College of Medical Genetics and Genomics," *Genetics in Medicine* 15(7):575-586.

Pretto, D. et al. (Sep. 17, 2014). "Clinical and Molecular Implications of Mosaicism in FMR1 Full Mutations," *Frontiers in Genetics* 5(Article318):1-11.

Saavedra-Matiz, C.A. et al. (Jul. 2013; e-published on Mar. 18, 2013). "Cost-Effective and Scalable DNA Extraction Method from Dried Blood Spots," *Clinical Chemistry* 59(7):1045-1051.

Saluto, A. et al. (Nov. 2005). "An Enhanced Polymerase Chain Reaction Assay to Detect Pre- and Full Mutation Alleles of the Fragile X Mental Retardation 1 Gene," *Journal of Molecular Diagnostics* 7(5):605-612.

Saul, R. et al. (Jun. 16, 1998). "FMR1-Related Disorders," in *GeneReviews*, R. Pagon et al., eds., University of Washington, Seattle, WA, twenty eight pages.

Tassone, F. (Mar. 2014). "Newborn Screening for Fragile X Syndrome," *JAMA Neurology* 71(3):355-359.

Tassone, F. et al. (Dec. 21, 2012). "FMR1 CGG Allele Size and Prevalence Ascertained Through Newborn Screening in the United States," *Genome Medicine* 4(12)(100):1-13.

Tassone, F. et al. (Jan. 2008). "A Rapid Polymerase Chain Reaction-Based Screening Method for Identification of All Expanded Alleles of the Fragile X (FMR1) Gene in Newborn and High-Risk Populations," *Journal of Molecular Diagnostics* 10(1):43-49.

Thierry-Mieg, N. (2006; e-published on Jan. 19, 2006). "A New Pooling Strategy for High-Throughput Screening: The Shifted Transversal Design," *BMC Bioinformatics* 7:28, thirteen pages.

Asuragen, Inc. (Feb. 2016). "AmplideX® PCR/CE FMR1 Reagents—Protocol Guide," twenty four pages.

Grasso, M. et al. (Jan. 2014). "A Novel Methylation PCR that Offers Standardized Determination of FMR1 Methylation and CGG Repeat Length without Southern Blot Analysis," *The Journal of Molecular Diagnostics* 16(1):23-31.

AUTOMATED NUCLEIC ACID REPEAT COUNT CALLING METHODS

CROSS-REFERENCE TO RELATED APPLICATIONS

This application claims priority to U.S. Provisional Ser. No. 61/903,847, filed on Nov. 13, 2013, entitled "AUTOMATED NUCLEIC ACID REPEAT COUNT CALLING METHODS," and U.S. Provisional Ser. No. 61/904,439, filed on Nov. 14, 2013, entitled "AUTOMATED NUCLEIC ACID REPEAT COUNT CALLING METHODS," which are hereby incorporated by reference in their entirety for all purposes.

FIELD

The following disclosure relates generally to determining genotypes and, more specifically, to determining genotypes associated with nucleic acid repeats.

BACKGROUND

Nucleic acid repeats are associated with various diseases. For example, expansion of a CGG triplet repeat sequence in the 5' UTR of the FMR1 gene (OMIM *309550) is associated with fragile X syndrome (FXS, OMIM #300624), the most common inherited form of mental retardation. Expansion of this repeat into the full mutation range ($\geq 200$ repeats) triggers methylation and transcriptional silencing of FMR1, causing FXS. In the "normal" range (5-44 repeats), the repeat sequence is stable between generations; intermediate alleles (45-54 repeats) require at least two generations to expand to full mutations, and premutation alleles (55-200 repeats) may expand to full mutations when passed from a mother to her child. Due to the difficulty of amplifying long triplet repeats, traditional tests for FXS carrier status have relied on Southern blotting to detect expanded CGG repeats. Recent advances in polymerase chain reaction (PCR) methods allow detection of these repeats with accuracy and sensitivity equal to Southern blotting. Capillary electrophoresis of the PCR product makes it possible to quantify the CGG repeat count, but requires laborious peak-calling and counting.

SUMMARY

The present disclosure relates to processes for determining the number of nucleic acid repeats (e.g., CGG repeats) in a DNA fragment comprising a nucleic acid repeat region (e.g., a CGG-rich region). One example method may include receiving DNA size and abundance data generated by resolving DNA amplification products. A set of low-pass data may be generated by applying a low-pass filter to the DNA size and abundance data and a set of band-pass data may be generated by applying a band-pass filter to the DNA size and abundance data. One or more peaks of the DNA size and abundance data representative of a number of nucleic acid repeats in the DNA may be identified based on peaks identified from the low-pass data and the band-pass data.

Thus, the present disclosure in one aspect provides methods of determining the number of nucleic acid repeats in a DNA fragment comprising a nucleic acid repeat region. These methods may include separating high frequency signals for DNA sequences from low frequency signals to de-convolve mixed primer signals.

In another aspect, there are provided methods of determining a genotype associated with a disease that involves nucleic acid repeats in an individual. Such methods are useful, for example, for assessing the risk of the individual as a carrier of a disease allele, as well as the likelihood of the individual to have a child having such diseases.

Systems and non-transitory computer-readable storage media for performing these processes are also provided.

All references described herein are incorporated by reference in their entirety.

DETAILED DESCRIPTION

Methods of Counting Nucleic Acid Repeats

Figure 1:
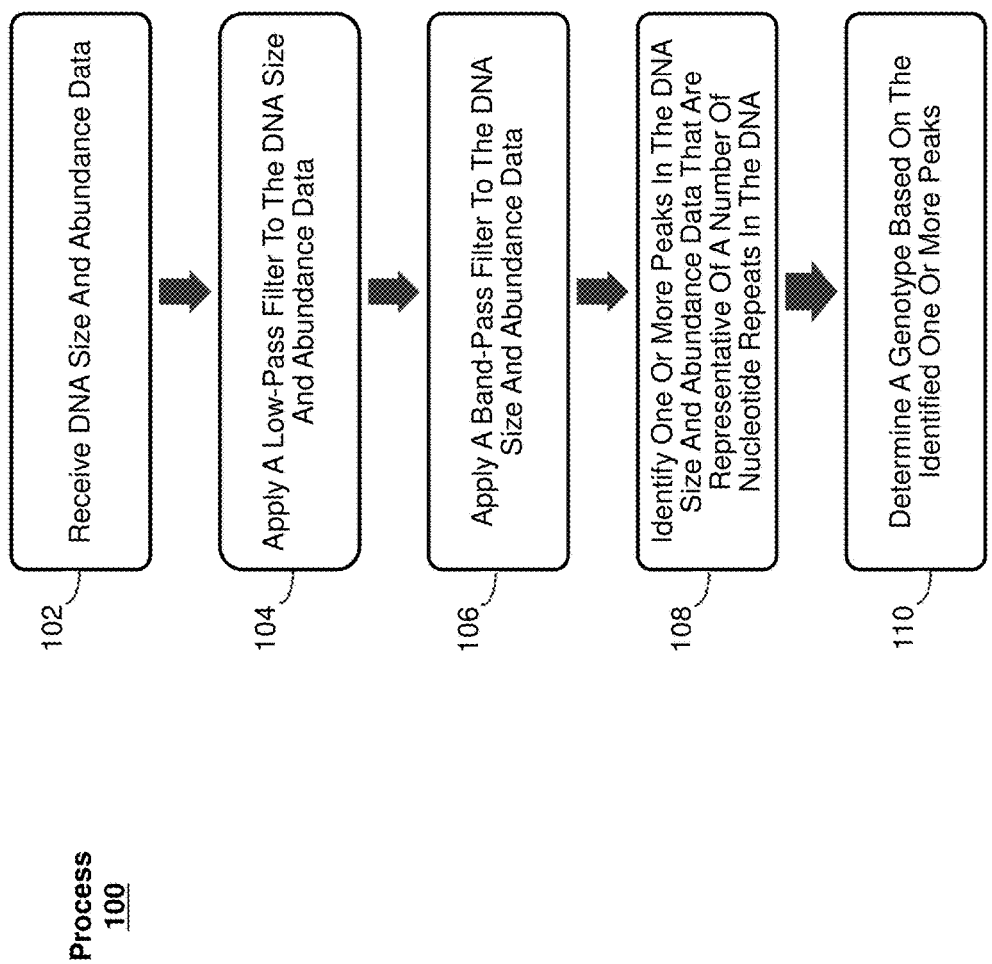
FIG. 1 illustrates an exemplary process for determining a number of repeats of a nucleotide sequence in a gene according to various examples.

The present disclosure in one aspect provides computer-implemented methods of determining the number of nucleic acid repeats in a DNA fragment comprising a nucleic acid repeat region. In some embodiments, there is provided a computer-implemented method of determining the number of nucleic acid repeats in a DNA fragment comprising a nucleic acid repeat region, the method comprising: a) applying a low pass filter and a band-pass filter to DNA size and abundance data of DNA amplification products generated from the DNA fragment comprising the nucleic acid repeat region by using a primer set comprising a first primer recognizing the nucleic acid repeat region and a second primer recognizing a region outside of the nucleic acid repeat region to generate a set of low-pass data and a set of band-pass data, and b) identifying one or more final peaks based on the low-pass data and the band-pass data, wherein the one or more final peaks represent the number of nucleic acid repeats in the nucleic acid repeat region. In some embodiments, the primer set further comprises a third primer recognizing a region outside of the nucleic acid repeat region that is on the opposite side of the region recognized by the second primer, wherein the second primer and the third primer allow amplification of the region comprising the entire nucleic acid repeat region. In some embodiments, the nucleic acid repeat is a repeat of 2, 3, 4, 5, 6, 7, 8, 9, 10, or more nucleotides. In some embodiments, the nucleic acid repeat is a trinucleotide repeat, including, but not limited to, CGG, GCC, GAA, CTG, and CAG.

In some embodiments, there is provided a computer-implemented method for determining the number of nucleic acid repeats in a DNA fragment comprising nucleic acid repeat region, the method comprising: a) receiving, by one or more processors, DNA size and abundance data of DNA amplification products generated from the DNA fragment comprising the nucleic acid repeat region by using a primer set comprising a first primer recognizing the nucleic acid repeat region and a second primer recognizing a region outside of the nucleic acid repeat region; b) generating, by the one or more processors, a set of sample data by sampling the DNA size and abundance data at a sampling frequency; c) generating, by the one or more processors, a set of low-pass data by applying a low-pass filter to the set of sample data; d) generating, by the one or more processors, a set of band-pass data by applying a band-pass filter to the set of sample data; e) identifying, by the one or more processors, one or more peaks in the low-pass data; f) identifying, by the one or more processors, one or more peaks in the band-pass data; and g) identifying, by the one or more processors, a final peak representing a number of nucleic acid repeats based on the one or more peaks in the low-pass data and the one or more peaks in the band-pass data. In some embodiments, the primer set further comprises a third primer recognizing a region outside of the nucleic acid repeat region that is on the opposite side as the region recognized by the second primer, wherein the second primer and the third primer allow amplification of a region comprising the entire nucleic acid repeat region.

In some embodiments, there is provided a computer-implemented method for determining the number of CGG repeats in a DNA fragment comprising a CGG-rich region, the method comprising: a) receiving, by one or more processors, DNA size and abundance data of DNA amplification products generated from the DNA fragment comprising the CGG-rich region by using a primer set comprising a first primer recognizing the CGG-rich region and a second primer recognizing a region outside of the CGG-rich region; b) generating, by the one or more processors, a set of sample data by sampling the DNA size and abundance data at a sampling frequency; c) generating, by the one or more processors, a set of low-pass data by applying a low-pass filter to the set of sample data; d) generating, by the one or more processors, a set of band-pass data by applying a band-pass filter to the set of sample data; e) identifying, by the one or more processors, one or more peaks in the low-pass data; f) identifying, by the one or more processors, one or more peaks in the band-pass data; and g) identifying, by the one or more processors, a final peak representing a number of CGG repeats in the DNA fragment comprising the CGG-rich region based on the one or more peaks in the low-pass data and the one or more peaks in the band-pass data. In some embodiments, the primer set further comprises a third primer recognizing a region outside of the CGG-rich region that is on the opposite side as the region recognized by the second primer, wherein the second primer and the third primer allow amplification of a region comprising the entire nucleic acid repeat region.

In some embodiments according to any of the methods above, the method further comprises resolving the DNA amplification products to generate the DNA size and abundance data prior to step a). The resolving can be carried out, for example, by capillary electrophoresis. In some embodiments, an electropherogram is produced by the capillary electrophoresis.

In some embodiments according to any of the methods above, the method further comprises converting, by the one or more processors, the DNA size and abundance data from a sampling (e.g., time) domain to a base-pair length domain prior to step b). In some embodiments, a DNA ladder is used to convert the DNA size and abundance data from the time domain to the base-pair length domain.

In some embodiments, the sampling frequency is equal to any of 2, 3, 4, 5, 6, or more samples per base-pair.

In some embodiments according to any of the methods above, generating the set of sample data by sampling the DNA size and abundance data at the sampling frequency comprises: generating a linear interpolation of the DNA size and abundance data; and sampling the linear interpolation of the DNA size and abundance data at the sampling frequency. In other embodiments, generating the set of sample data by sampling the DNA size and abundance data at the sampling frequency comprises: generating a cubic spline interpolation of the DNA size and abundance data; and sampling the cubic spline interpolation of the DNA size and abundance data at the sampling frequency. In yet other embodiments, generating the set of sample data by sampling the DNA size and abundance data at the sampling frequency comprises: generating a zero-order hold/nearest neighbor interpolation of the DNA size and abundance data; and sampling the zero-order hold/nearest neighbor interpolation of the DNA size and abundance data at the sampling frequency.

In some embodiments according to any of the methods above, the band-pass filter has a low cutoff frequency of 1/13 multiplied by the Nyquist frequency (e.g., two times the sampling frequency) and a high cutoff frequency of 1/11 multiplied by the Nyquist frequency. In other embodiments according to any of the methods above, the band-pass filter may have a low cutoff frequency of any of 1/14, 1/15, 1/16, or 1/17 multiplied by the Nyquist frequency and a high cutoff frequency of any of 1/10, 1/9, 1/8, or 1/7 multiplied by the Nyquist frequency. Other frequencies may be used depending on the sampling frequency and the period of the nucleic acid repeats.

In some embodiments according to any of the methods above, the low-pass filter has a cutoff frequency of $5.0*10^{-6}$ multiplied by the Nyquist frequency. In other embodiments according to any of the methods above, the low-pass filter may have a cutoff frequency between $8.0*10^{-6}$ and $2.0*10^{-6}$ multiplied by the Nyquist frequency, such as any of $8.0*10^{-6}$, $7.0*10^{-6}$, $6.0*10^{-6}$, $4.0*10^{-6}$, $3.0*10^{-6}$, or $2.0*10^{-6}$ multiplied by the Nyquist frequency.

In some embodiments according to any of the methods above, the low-pass filter and the band-pass filter are zero-phase finite impulse response (FIR) filters implemented using a Hamming window.

In some embodiments according to any of the methods above, the set of sample data comprises a signal representing a combination of a nucleic acid repeat series (such as CGG series) of the nucleic acid repeat region (such as CGG-rich region) and a full-length amplicon of the DNA fragment comprising the nucleic acid repeat region (such as the CGG-rich region), the set of band-pass data comprises a signal representing the nucleic acid repeat series (such as the CGG series) of the nucleic acid repeat region (such as the CGG-rich region), and the set of low-pass data comprises a signal representing the full-length amplicon of the DNA fragment comprising the nucleic acid repeat region (such as the CGG-rich region).

In some embodiments according to any of the methods above, identifying the final peak representing the number of nucleic acid repeats (such as CGG repeats) in the DNA fragment comprising the nucleic acid repeat region (such as CGG-rich region) comprises one or more steps of: removing peaks from the one or more peaks in the low-pass data having a width less than 4.5 base-pairs and a height less than a threshold value; removing peaks from the one or more peaks in the band-pass data having a width less than 4.5 base-pairs and a height less than the threshold value; removing peaks from the one or more peaks in the band-pass data having a height less than a height of an adjacent peak having a larger base-pair length; in response to a peak of the one or more peaks in the low-pass data having a height less than a height of a peak of the one or more peaks in the band-pass data that is within 3 base-pairs of the peak of the one or more peaks in the low-pass data, setting a center of the peak of the one or more peaks in the low-pass data to a center of the peak of the one or more peaks in the band-pass data, and setting a boundary of the peak of the one or more peaks in the low-pass data to a union of the peak of the one or more peaks in the low-pass data and the peak of the one or more peaks in the band-pass data; merging peaks of the one or more peaks in the low-pass data and the one or more peaks in the band-pass data that have base-pair lengths greater than 165 base-pairs and that are within 30 base-pairs of each other; and merging peaks of the one or more peaks in the low-pass data and the one or more peaks in the band-pass data that are within 15 base-pairs and that are more than a factor of 2 different in height, wherein a remaining peak of the one or more peaks in the low-pass data is the final peak.

In some embodiments, the DNA fragment comprises a CGG-rich region. In some embodiments, the DNA fragment comprising a CGG-rich region is the 5'-UTR of the fragile X mental retardation 1 gene (FMR1). In some embodiments, the DNA fragment comprising a CGG-rich region is the 5'-UTR of the fragile X mental retardation 2 gene (FMR2). In some embodiments, the first primer comprises at least 1, 2, 3, 4, 5, 6, 7, or 8 CGG or CCG repeats.

In some embodiments, the DNA fragment comprises a CAG-rich region. In some embodiments, the DNA fragment comprising a CAG-rich region is in the coding region of a protein. In some embodiments, the first primer comprises at least 1, 2, 3, 4, 5, 6, 7, or 8 CAG or CTG repeats.

Methods of Determining Genotypes Associated with Diseases

In some embodiments, there is provided a computer-implemented method for determining a genotype associated with a disease (such as genetic disease) that involves nucleic acid repeats in an individual, the method comprising: a) performing DNA amplification reaction using a primer set comprising a first primer recognizing the nucleic acid repeat region on the disease gene and a second primer recognizing a region outside of the nucleic acid repeat region on the disease gene; b) resolving the DNA amplification products to obtain DNA size and abundance data; c) applying a low-pass filter and a band-pass filter to the DNA size and abundance data to identify a peak representing the number of nucleic acid repeats in the nucleic acid repeat-containing region on the disease gene; and d) determining the genotype of the individual based on the identified peak. In some embodiments, the primer set further comprises a third primer recognizing a region outside of the nucleic acid repeat region that is on the opposite side as the region recognized by the second primer, wherein the second primer and the third primer allow amplification of the region comprising the entire nucleic acid repeat region.

In some embodiments, there is provided a computer-implemented method for determining a genotype associated with Fragile X syndrome in an individual, the method comprising: a) performing DNA amplification reaction using a primer set comprising a first primer recognizing the CGG-rich region on the 5'UTR of the FMR1 gene and a second primer recognizing a region outside of the CGG-rich region on the 5'UTR of the FMR1 gene; b) resolving the DNA amplification products to obtain DNA size and abundance data; c) applying a low-pass filter and a band-pass filter to the DNA size and abundance data to identify a peak representing a number of CGG repeats in the CGG-rich region on the 5'UTR of the FMR1 gene; and d) determining the genotype of the individual based on the identified peak. In some embodiments, the primer set further comprises a third primer recognizing a region outside of the CGG-rich region that is on the opposite side as the region recognized by the second primer, wherein the second primer and the third primer allow amplification of the region comprising the entire CGG-rich region.

In some embodiments according to any of the methods above, resolving is carried out by capillary electrophoresis and may produce an electropherogram.

In some embodiments according to any of the methods above, the method further comprises converting, by the one or more processors, the DNA size and abundance data from a sampling (e.g., time) domain to a base-pair length domain prior to step c).

In some embodiments according to any of the methods above, a DNA ladder is used to convert the DNA size and abundance data from the time domain to the base-pair length domain.

In some embodiments according to any of the methods above, the method further comprises sampling the DNA size and abundance data at a sampling frequency, and wherein applying the low-pass filter and the band-pass filter to the DNA size and abundance data comprises applying the low-pass filter and the band-pass filter to the sampled DNA size and abundance data.

In some embodiments according to any of the methods above, the sampling frequency is equal to any of 2, 3, 4, 5, 6, or more samples per base-pair.

In some embodiments according to any of the methods above, generating the set of sample data by sampling the DNA size and abundance data at the sampling frequency comprises: generating a linear interpolation of the DNA size and abundance data; and sampling the linear interpolation of the DNA size and abundance data at the sampling frequency. In other embodiments, generating the set of sample data by sampling the DNA size and abundance data at the sampling frequency comprises: generating a cubic spline interpolation of the DNA size and abundance data; and sampling the cubic spline interpolation of the DNA size and abundance data at the sampling frequency. In yet other embodiments, generating the set of sample data by sampling the DNA size and abundance data at the sampling frequency comprises: generating a zero-order hold/nearest neighbor interpolation of the DNA size and abundance data; and sampling the zero-order hold/nearest neighbor interpolation of the DNA size and abundance data at the sampling frequency.

In some embodiments according to any of the methods above, the band-pass filter has a low cutoff frequency of 1/13 multiplied by the Nyquist frequency (e.g., two times the sampling frequency) and a high cutoff frequency of 1/11 multiplied by the Nyquist frequency. In other embodiments according to any of the methods above, the band-pass filter may have a low cutoff frequency of any of 1/14, 1/15, 1/16, or 1/17 multiplied by the Nyquist frequency and a high cutoff frequency of any of 1/10, 1/9, 1/8, or 1/7 multiplied by the Nyquist frequency. Other frequencies may be used depending on the sampling frequency and the period of the nucleic acid repeats.

In some embodiments according to any of the methods above, the low-pass filter has a cutoff frequency of $5.0*10^{-6}$ multiplied by the Nyquist frequency. In other embodiments according to any of the methods above, the low-pass filter may have a cutoff frequency between $8.0*10^{-6}$ and $2.0*10^{-6}$ multiplied by the Nyquist frequency, such as any of $8.0*10^{-6}$, $7.0*10^{-6}$, $6.0*10^{-6}$, $4.0*10^{-6}$, $3.0*10^{-6}$, or $2.0*10^{-6}$ multiplied by the Nyquist frequency.

In some embodiments according to any of the methods above, the low-pass filter and the band-pass filter are zero-phase finite impulse response (FIR) filters implemented using a Hamming window.

In some embodiments according to any of the methods above, the DNA size and abundance data comprises a signal representing a combination of a CGG series of the FMR1 gene and a full-length amplicon of the 5' UTR of the FMR1 gene, the set of band-pass data comprises a signal representing the CGG series of the FMR1 gene, and the set of low-pass data comprises a signal representing the full-length amplicon of the 5' UTR of the FMR1 gene.

In some embodiments according to any of the methods above, identifying the peak representing the number of CGG repeats in the CGG-rich region on the 5'UTR of the FMR1 gene comprises: removing peaks from the one or more peaks in an output of the low-pass filter having a width less than 4.5 base-pairs and a height less than a threshold value; removing peaks from the one or more peaks in an output of the band-pass filter data having a width less than 4.5 base-pairs and a height less than the threshold value; removing peaks from the one or more peaks in the output of the band-pass filter having a height less than a height of an adjacent peak having a larger base-pair length; in response to a peak of the one or more peaks in the output of the low-pass filter having a height less than a height of a peak of the one or more peaks in the output of the band-pass filter that is within 3 base-pairs of the peak of the one or more peaks in the output of the low-pass filter, setting a center of the peak of the one or more peaks in the output of the low-pass filter to a center of the peak of the one or more peaks in the output of the band-pass filter, and setting a boundary of the peak of the one or more peaks in the output of the low-pass filter to a union of the peak of the one or more peaks in the output of the low-pass filter and the peak of the one or more peaks in the output of the band-pass filter; merging peaks of the one or more peaks in the output of the low-pass filter and the one or more peaks in the output of the band-pass filter that have base-pair lengths greater than 165 base-pairs and that are within 30 base-pairs of each other; and merging peaks of the one or more peaks in the output of the low-pass filter and the one or more peaks in the output of the band-pass filter that are within 15 base-pairs and that are more than a factor of 2 different in height, wherein a remaining peak of the one or more peaks in the output of the low-pass filter is the final peak.

Determination of Carrier for Nucleic Acid Repeat Disorders

The methods described above are useful for determining whether an individual is a carrier for a disease (such as genetic disease) involving nucleic acid repeats (referred to herein as "nucleic acid repeat disorders").

In some embodiments, the nucleic acid repeat disorder is selected from the group consisting of fragile X, Friedreich's ataxia, myotonic dystrophy, DRPLA (Dentatorubropallidoluysian atrophy), HD (Huntington's disease), SBMA (Spinobulbar muscular atrophy or Kennedy disease), SCA1 (Spinocerebellar ataxia Type 1), SCA2 (Spinocerebellar ataxia Type 2), SCA3 (Spinocerebellar ataxia Type 3 or Machado-Joseph disease), SCA6 (Spinocerebellar ataxia Type 6), SCAT (Spinocerebellar ataxia Type 7), SCA17 (Spinocerebellar ataxia Type 17), and spinocerebellar ataxia.

In some embodiments, the nucleic acid repeat disorder is a trinucleotide repeat disorder. Trinucleotide repeat disorders (also known as trinucleotide repeat expansion disorders, triplet repeat expansion disorders or codon reiteration disorders) are a set of genetic disorders caused by trinucleotide repeat expansion, a kind of mutation where trinucleotide repeats in certain genes exceed the normal, stable threshold, which differs per gene. The mutation is a subset of unstable microsatellite repeats that occur throughout all genomic sequences. If the repeat is present in a healthy gene, a dynamic mutation may increase the repeat count and result in a defective gene. In some embodiments, the trinucleotide repeat order involves CAG repeats, for example polyglutamine (polyQ diseases). Currently, there are at least nine neurologic disorders are known to be caused by an increased number of CAG repeats, typically in coding regions of otherwise unrelated proteins. During protein synthesis, the expanded CAG repeats are translated into a series of uninterrupted glutamine residues forming what is known as a polyglutamine tract ("polyQ"). Such polyglutamine tracts may be subject to increased aggregation. Various poly Q diseases and the pathogenic repeat thresholds are provided in Table 1.

TABLE 1

Polyglutamine (PolyQ) Diseases

| Type | Gene | Normal PolyQ repeats | Pathogenic PolyQ repeats |
| --- | --- | --- | --- |
| DRPLA (Dentatorubropallidoluysian atrophy) | ATN1 or DRPLA | 6-35 | 49-88 |
| HD (Huntington's disease) | HTT (Huntingtin) | 10-35 | 35+ |
| SBMA (Spinobulbar muscular atrophy or Kennedy disease) | Androgen receptor on the X chromosome. | 9-36 | 38-62 |
| SCA1 (Spinocerebellar ataxia Type 1) | ATXN1 | 6-35 | 49-88 |
| SCA2 (Spinocerebellar ataxia Type 2) | ATXN2 | 14-32 | 33-77 |
| SCA3 (Spinocerebellar ataxia Type 3 or Machado-Joseph disease) | ATXN3 | 12-40 | 55-86 |
| SCA6 (Spinocerebellar ataxia Type 6) | CACNA1A | 4-18 | 21-30 |
| SCA7 (Spinocerebellar ataxia Type 7) | ATXN7 | 7-17 | 38-120 |
| SCA17 (Spinocerebellar ataxia Type 17) | TBP | 25-42 | 47-63 |

In some embodiments, the trinucleotide repeat order involves CGG repeats, for example fragile X syndrome and fragile X-associated tremor/ataxia syndrome. In some embodiments, the trinucleotide repeat disorder involves GCC disorder, for example fragile XE mental retardation. In some embodiments, the trinucleotide repeat disorder involves GAA repeats, for example Friedreich's ataxia. In some embodiments, the trinucleotide repeat disorder involves CTG repeats, for example myotonic dystrophy or spinocerebellar ataxia type 8. In some embodiments, the trinucleotide repeat disorder involves three nucleotides at the 5' end, such as spinocerebellar ataxia type 12. Various diseases and the pathogenic repeat thresholds are provided in Table 2.

TABLE 2

| Type | Gene | Codon | Normal/ wildtype | Pathogenic |
|---|---|---|---|---|
| FRAXA (Fragile X syndrome) | FMR1, on the X-chromosome | CGG | 6-53 | 230+ |
| FXTAS (Fragile X-associated tremor/ataxia syndrome) | FMR1, on the X-chromosome | CGG | 6-53 | 55-200 |
| FRAXE (Fragile XE mental retardation) | AFF2 or FMR2, on the X-chromosome | GCC | 6-35 | 200+ |
| FRDA (Friedreich's ataxia) | FXN or X25, (frataxin-reduced expression) | GAA | 7-34 | 100+ |
| DM (Myotonic dystrophy) | DMPK | CTG | 5-37 | 50+ |
| SCA8 (Spinocerebellar ataxia Type 8) | OSCA or SCA8 | CTG | 16-37 | 110-250 |
| SCA12 (Spinocerebellar ataxia Type 12) | PPP2R2B or SCA12 | CAG | 4-32 | 66-78 |

In some embodiments, the method comprises determining whether the individual is a carrier for fragile X syndrome based on the genotype of the individual, wherein a number of CGG repeats in the CGG-rich region on the 5'UTR of the FMR1 gene between 5-44 repeats is indicative of a normal allele, a number of CGG repeats in the CGG-rich region on the 5'UTR of the FMR1 gene between 45-54 repeats is indicative of a an intermediate allele, a number of CGG repeats in the CGG-rich region on the 5'UTR of the FMR1 gene between 55-200 repeats is indicative of a premutation allele, and wherein a number of CGG repeats in the CGG-rich region on the 5'UTR of the FMR1 gene greater than 200 repeats is indicative of a full mutation allele.

In some embodiments, the method comprises determining whether the individual is a carrier for Huntington's disease based on the genotype of the individual, wherein a number of CAG repeats in the CAG-rich region on coding region of the HTT gene of less than about 35 repeats is indicative of a normal allele, a number of CAG repeats in the CAG-rich region on coding region of the HTT gene between 36-60 repeats is indicative of a reduced penetrance allele, and a number of CAG repeats in the CAG-rich region on coding region of the HTT gene of more than about 40 repeats is indicative of a full penetrance allele.

Methods of Diagnosing a Disease that Involves a Nucleic Acid Repeat

In some embodiments, there are provided methods of diagnosing a disease that involves a nucleic acid repeat by using any one of the methods described herein.

Methods of Amplifying DNA from a DNA Comprising Nucleic Repeat Region

Methods of amplifying DNA from a DNA comprising a nucleic acid repeat region are known in the art, and have been reported in, for example, Chen et al. An Information-Rich CGG Repeat Primed PCR That Detects the Full Range of Fragile X Expanded Alleles and Minimizes the Need for Southern Blot Analysis. Journal of Molecular Diagnostics (2010) vol. 12 (5) pp. 589-600; Alessandro Saluto et al. An Enhanced Polymerase Chain Reaction Assay to Detect Pre- and Full Mutation Alleles of the Fragile X Mental Retardation 1 Gene. Journal of Molecular Diagnostics (2005) vol. 7 (5) pp. 605-612; Feras M. Hantash et al. Qualitative assessment of FMR1 (CGG)n triplet repeat status in normal, intermediate, premutation, full mutation, and mosaic carriers in both sexes: Implications for fragile X syndrome carrier and newborn screening. Genetics in Medicine (2010) 12:162-173; Stela Flilipovic-Sadic et al. A Novel FMR1 PCR Method for the Routine Detection of Low Abundance Expanded Alleles and Full Mutations in Fragile X Syndrome. Clinical Chemistry (2010) vol. 56 (3) pp. 399-408; and Flora Tassone et al. A rapid polymerase chain reaction-based screening method for identification of all expanded alleles of the fragile X (FMR1) gene in newborn and high-risk populations. Journal of Molecular Diagnostics (2008) vol. 10(1) pp. 43-49, the content of each of which are incorporated by reference in their entirety. Methods of amplifying nucleic acid repeat regions are also described in, for example, U.S. Pat. Nos. 7,855,053, 8,409,805, and U.S. Patent Publication No. 2010/0243451, the content of each of which is incorporated herein by reference in their entirety.

In some embodiments, the first primer comprises at least 1, 2, 3, 4, 5, 6, 7, or 8 CGG or CCG repeats. In some embodiments, the first primer further comprises non-CGG repeat residues that are 5' to the CCG region. In some embodiments, the first primer further comprises non-CGG repeat residues that are 3' to the CCG region.

Exemplary Methods

In the following description of the disclosure and examples, reference is made to the accompanying drawings in which it is shown by way of illustration specific examples that can be practiced. It is to be understood that other examples can be practiced and structural changes can be made without departing from the scope of the disclosure.

The present disclosure relates to processes for determining the number of CGG repeats in a DNA comprising a CGG-rich region. One example method may include receiving DNA size and abundance data generated by resolving DNA amplification products. A set of low-pass data may be generated by applying a low-pass filter to the DNA size and abundance data and a set of band-pass data may be generated by applying a band-pass filter to the DNA size and abundance data. A peak of the DNA size and abundance data representative of a number of CGG repeats in the DNA may be identified based on peaks identified from the low-pass data and the band-pass data.

FIG. 1 illustrates an exemplary process 100 for determining a number of nucleotide repeats in a gene according to various examples. Process 100 will be described herein as determining a number of CGG repeats in a deoxyribonucleic acid (DNA) comprising a CGG-rich region. However, it should be appreciated that process 100 may similarly be used to determine a number of any desired nucleotide sequence in any desired gene to identify any type of nucleic acid repeat disorder.

At block 102, DNA size and abundance data may be received by one or more processors of a computing device. The size and abundance data may be generated by resolving DNA amplification products using capillary electrophoresis (e.g., to produce an electropherogram) or the like. The DNA amplification products may be generated from the DNA using a primer set including a first primer recognizing the CGG-rich region, a second primer recognizing a region outside of the CGG-rich region, and a third primer recognizing a region outside of the CGG-rich region that is on a side opposite the region recognized by the second primer. The first primer may include four or more CGG or CCG repeats and may further include sequences outside of the CGG-rich region (e.g., A or T residing within or at the end of the part of the primer that anneals to the CGG repeat sequences). In some examples, the DNA comprising the CGG-rich region may include the 5'-UTR of the fragile X mental retardation 1 gene (FMR1). In these examples, the first primer may recognize the CGG-rich region on the 5'-UTR of the FMR1 gene, and the second and third primers may recognize regions outside and on opposite sides of the CGG-rich region on the 5'-UTR of the FMR1 gene. In other examples, the DNA comprising the CGG-rich region may include the 5'-UTR of the fragile X mental retardation 2 gene (FMR2). In these examples, the first primer may recognize the CGG-rich region on the 5'-UTR of the FMR2 gene, and the second and third primers may recognize regions outside and on opposite sides of the CGG-rich region on the 5'-UTR of the FMR2 gene. It should be appreciated that other genes may be represented by the DNA size and abundance data.

In some examples, the DNA size and abundance data may include multiple data points having a fluorescence value and an associated time at which the data point sample was taken. In these examples, the DNA size and abundance data may be transformed from the time domain to a base-pair length domain. This may be accomplished using a DNA ladder having fragments of known length and by converting the DNA size and abundance data x-value from machine sample time to base-pair length. In some examples, the DNA fragments corresponding to the individual's DNA may be labeled by a fluorescent dye, such as FAM, and the fragments corresponding to the DNA ladder may be labeled by a distinct fluorescent dye, such as ROX. In some examples, high FAM signal intensity may create crosstalk between fluorescent detection channels, adding spurious peaks or removing true ones, impeding automation detection of ROX ladder peaks. In these instances, a prior distribution on expected locations of ladder peaks may be used to match observed peaks to the prior using dynamic programming to simultaneously assign peaks and minimize the squared-deviation in peak location using the following formula:

$$\min\_dev(i, p) = \min\left[\min_{q=1}^{p-1}(\min\_dev(i-1, q) + \text{penalty}(i, p)),\right.$$
$$\left.\min_{q=1}^{p-1}(\min\_dev(i-2, q) + \text{penalty}(i, p)) + \text{MISSED\_PEAK\_PENALTY}\right]$$

$i$ indexes fragment sizes, $p$ indexes peaks

In some examples, the sampling interval of the machine used to generate the DNA size and abundance data may not be linear in base-pair length. In these examples, once the DNA size and abundance data is converted into the base-pair length domain, the DNA size and abundance data may be interpolated using linear interpolation, cubic spline interpolation, or zero-order hold/nearest neighbor interpolation, and sampled to a constant resolution. Any desired resolution may be used and, in one example, a sampling frequency of four samples per base-pair may be used. The result of the sampling may be a set of data or a signal having a first component representative of a CGG series of the CGG-rich region (e.g., of the 5' UTR of the FMR1 gene) and a second, gene-specific, component representative of the full-length amplicon (e.g., of the 5' UTR of the FMR1 gene). Since the first component is representative of a CGG series, it is expected to have a period of three base-pairs, or 12 samples. The second component, however, is expected to have a longer period or may not be periodic at all since the DNA size and abundance data is expected to include only one or a small number of full-length amplicons, depending on sample zygosity, that are unlikely to be separated by only one repeat.

Figure 2:
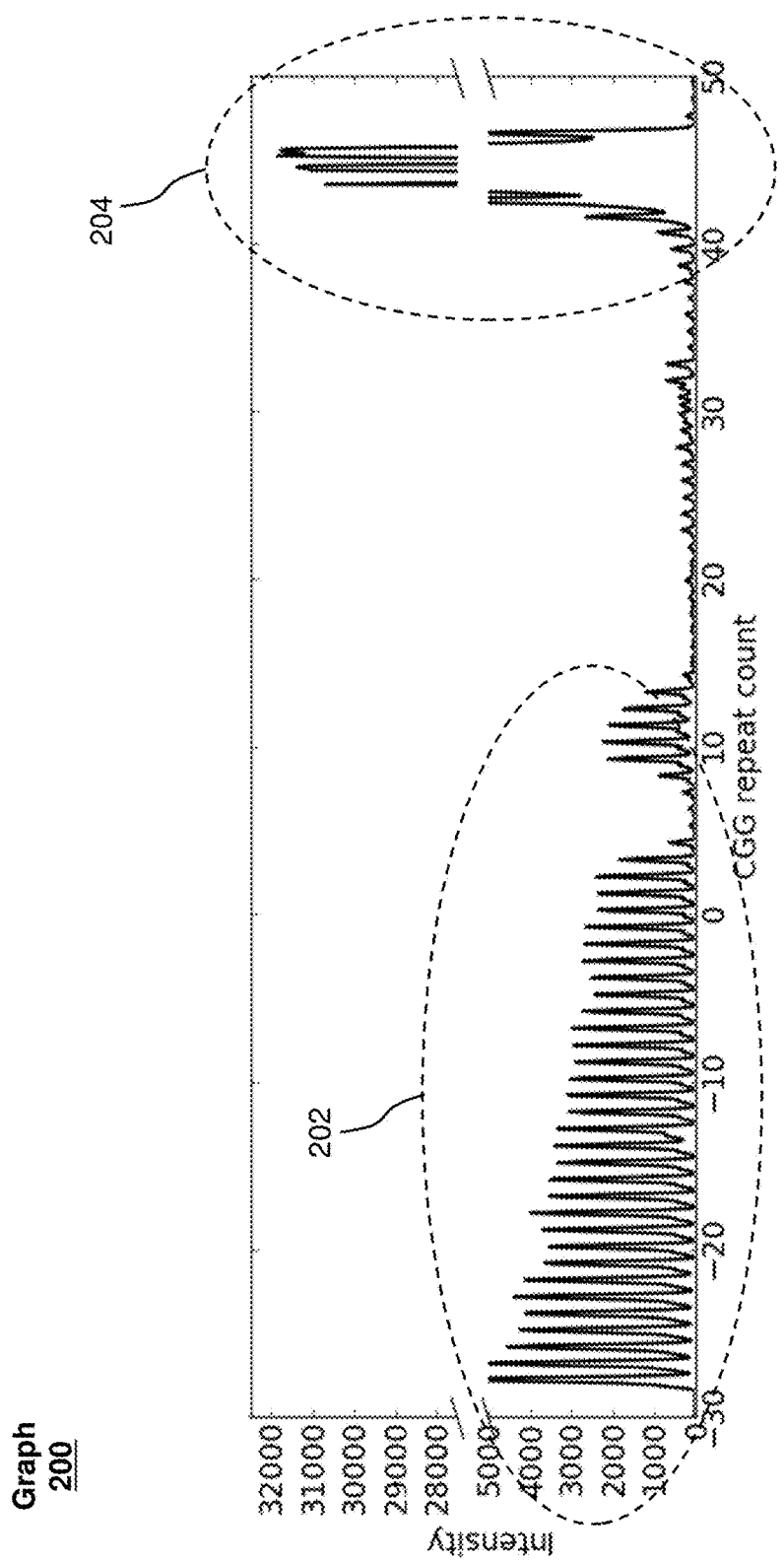
FIG. 2 illustrates a graph showing a signal or set of data generated by sampling an exemplary electrophoresis trace, with the X-axis normalized to CGG repeat count.

FIG. 2 illustrates graph 200 showing a signal or set of data generated by sampling an example electrophoresis trace, with the X-axis normalized to CGG repeat count. As shown, the set of data or signal includes a first section 202 attributable to the first component of the set of data or signal that is representative of a CGG series of the CGG-rich region having a decreasing series of periodic peaks corresponding to the successively longer CGG repeat sequences. For example, the initial peak (on the far left) may correspond to a $CGG_5$ repeat, the next peak to the right may correspond to the $CGG_6$ repeat, and so on. The peak amplitudes of the peaks in first section 202 may decrease as repeat length increases for partial copies due to decreasing efficiency of amplification. Graph 200 further shows the set of data or signal having a second section 204 attributable to the second component of the set of data or signal that is representative of the full-length amplicon.

Figure 3:
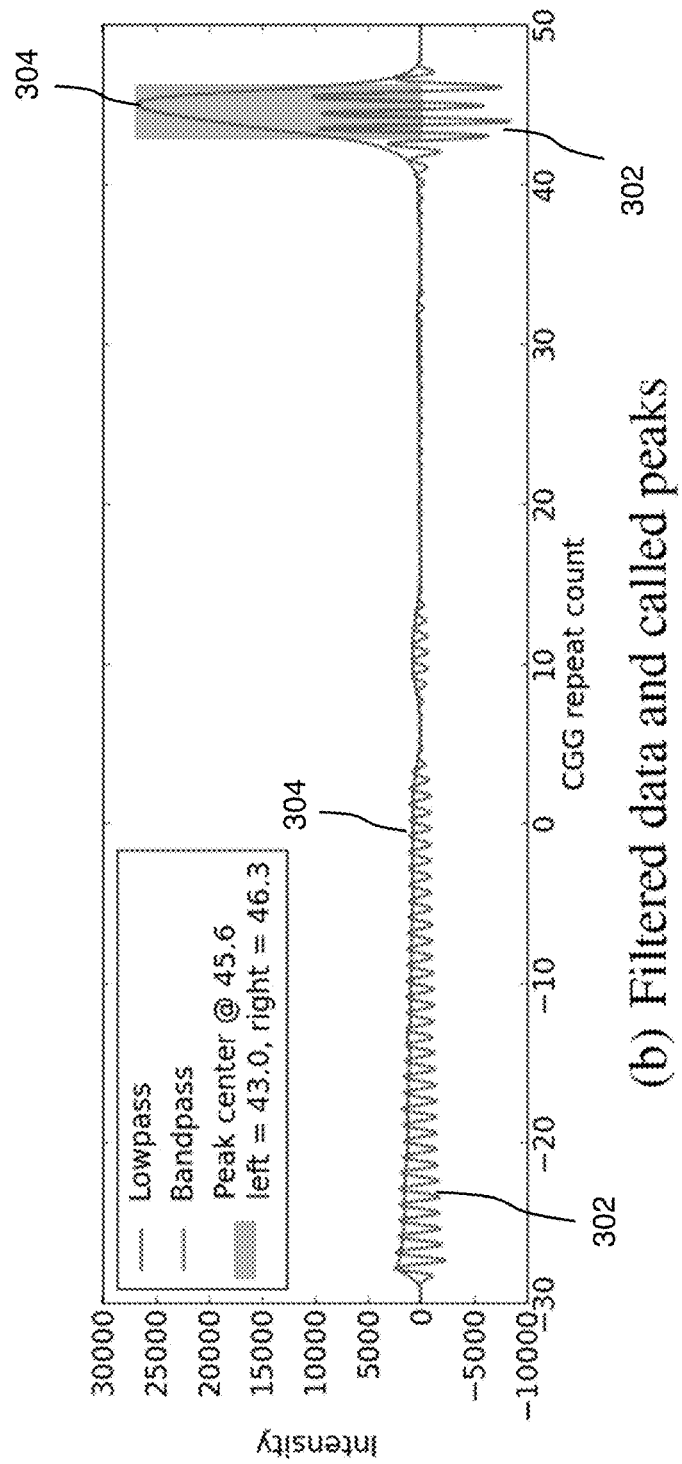
FIG. 3 illustrates a graph showing the result of low-pass and band-pass filtering the signal or set of data shown in FIG. 2.

Referring back to process 100 shown in FIG. 1, a low-pass filter may be applied to the DNA size and abundance data at block 104 to generate a set of low-pass data corresponding to the second component of the DNA size and abundance data that is representative of the full-length amplicon. As mentioned above, the period of the second component of the DNA size and abundance data may be longer than the period of the first component or may not be periodic at all. As such, a low-pass filter having a cutoff frequency higher than the frequency of the second component may be used to isolate the second component from the entire set of DNA size and abundance data. In some examples, a 24-tap, zero-phase finite impulse response (FIR) filter implemented using a Hamming window and having a cutoff frequency of $1.0*10^{-5}$ multiplied by the sampling frequency may be used. However, it should be appreciated that other types of low-pass filters having other cutoff frequencies determined empirically or through calculations may be used. FIG. 3 illustrates graph 300 showing the result of low-pass and band-pass (discussed below) filtering of the signal or set of data shown in FIG. 2. Specifically, graph 300 shows line 304 representing the result of low-pass filtering the signal or set of data shown in FIG. 2. As shown, line 304 includes a first small, initial increase in intensity that gradually decreases with increasing CGG repeat count and a second large peak centered at 45.6 CGG repeat count and having boundaries at 43.0 and 46.3 repeat counts. This larger peak may be representative and attributable to the full-length amplicon.

Referring back to process 100 shown in FIG. 1, a band-pass filter may be applied to the DNA size and abundance data at block 106 to generate a set of band-pass data corresponding to the first component of the DNA size and abundance data that is representative of the CGG series of the CGG-rich region. As mentioned above, the period of the first component of the DNA size and abundance data may three base-pairs, or 12 samples. Thus, the frequency at which the CGG repeat signal is expected to occur is 1/3 per base-pair. As such, a band-pass filter having cutoff frequencies enclosing this frequency may be used to isolate the first component from the entire set of DNA size and abundance data. In some examples, a 24-tap, zero-phase FIR filter implemented using a Hamming window and having a lower cutoff frequency of (1/13)*(2)*(sampling frequency used at block 102) and an upper cutoff frequency of (1/11)*(2)* (sampling frequency used at block 102) may be used. However, it should be appreciated that other types of band-pass filters having other cutoff frequencies determined empirically or through calculations may be used. Line 302 of graph 300, shown in FIG. 3, illustrates the result band-pass filtering the signal or set of data shown in FIG. 2. As shown, line 302 includes a small, decreasing periodic signal followed by a group of larger peaks corresponding in CGG repeat count with the large peak of line 304.

Referring back to process 100 shown in FIG. 1, at block 108, one or more peaks in the DNA size and abundance data that are representative of a number of nucleotide repeats in the DNA may be identified. In some examples, this may include identifying the peaks in the low-pass data generated at block 104 and identifying the peaks in the band-pass data generated at block 106. To identify the peaks, each signal or set of data (e.g., the low-pass data and the band-pass data), represented by the function $f$, may be interpolated using a cubic spline and the interpolated data may be used to approximate the first derivative $f'$ and the second derivative $f''$ of the signal or set of data $f$. Next, a root C of the first derivative $f'$ that also satisfies the condition that the second derivative at C $f''$ (C)<0 may be identified. This root C may be designated as the center of the corresponding peak. Values L and R may be the locations of roots of $f'$ that are adjacent (e.g., closest roots of $f'$ that have higher and lower CGG repeat counts) to the left and right, respectively, of root C. To compute the peak boundaries L' and R' for the peak centered at C, the following equations may be used:

$$L' = \min x \in [L, C] s.t. |f'(x)| > D$$

$$R' = \max x \in [C, R] s.t. |f'(x)| > D$$

In other words, the left peak boundary L' may be the smallest X-axis value (e.g., CGG repeat count) between adjacent root L and center C that has a first derivative $f'$ whose absolute value is greater than a cutoff D. The value of D may depend on the dynamic range of the DNA size and abundance data (and thus, on the sample protocol and hardware) and may be selected to be a value corresponding to the location that a human would identify as the peak boundary. Similarly, the right peak boundary R' may be the largest X-axis value (e.g., CGG repeat count) between center C and adjacent root R that has a first derivative $f'$ whose absolute value is greater than a cutoff D. This peak identification process may be performed for each root C of the first derivative $f'$ of each signal or set of data (e.g., the low-pass data and the band-pass data) that also satisfies the condition that the second derivative at C $f''$ (C)<0. In this way, each peak of the low-pass data and each peak of the high-pass data may be identified. While a specific peak detection algorithm is described above, it should be appreciated that other peak detection algorithms may be used.

Once the set of peaks in the low-pass data and the set of peaks in the band-pass data are identified, the peaks in each set may be filtered to remove peaks that have a high probability of being noise, rather than ones accurately reflecting the CGG series of the CGG-rich region or the full-length amplicon. In some examples, the peak filtering may include identifying thin peaks whose widths are less than a first threshold number of CGG repeats (e.g., 1.5) and whose heights are less than a machine-dependent second threshold. The exact values of these first and second thresholds may be determined and set empirically or through calculations to remove peaks resulting from noise. The identified thin peaks may be removed from their respective set of peaks (e.g., from the set of peaks of the low-pass data or from the set of peaks of the band-pass data), or may otherwise be identified (e.g., using a flag) as being noise. Peaks having heights that are smaller than the height of a peak immediately to their right (e.g., having larger CGG repeat counts) that are within the same set of data (e.g., within the low-pass data or within the band-pass data) may also be removed from their respective set of peaks or may otherwise be identified as being noise since it is expected that the height of each peak is to be less than the previous peak (e.g., to the left) due to the decreasing efficiency of amplification with increasing length.

In some examples, the low-pass filter may mistakenly exclude a full-length peak. Such excluded peaks may have a corresponding large peak in the band-pass data that is much larger than the other peaks from the band-pass data that represent the CGG series of the CGG-rich region. Thus, the peaks from the band-pass data may be used to adjust the low-pass peaks. Specifically, if a peak $P_L$ from the low-pass data is within a threshold number of CGG repeats (e.g., one repeat) of a peak $P_B$ from the band-pass data that larger than the peak $P_L$, the center of the low-pass peak $P_L$ peak may be set to the center of the band-pass peak $P_B$. The peak boundaries of the low-pass peak $P_L$ may also be set to the union of the low-pass peak $P_L$ and the band-pass peak $P_B$.

In some examples, some peaks may be merged if it is determined that one or more of the peaks are attributable to noise. The merging of peaks may include treating the two or more merged peaks as a single peak, meaning that the largest peak of the merged peaks may be treated as the true peak. In some examples, peaks within each set of data (e.g., within the low-pass data or within the band-pass data) having peaks above a threshold number (e.g., 55) of repeats may be merged if they are within a threshold number (e.g., 10) of repeats of each other. All peaks, regardless of repeat count, within the same set of data (e.g., within the low-pass data or within the band-pass data) may be merged if they are within a threshold number of repeats (e.g., 5) and more than a factor of 2 different in amplitude.

The resulting peak(s) in the low-pass data may be centered at a CGG repeat value corresponding to the number of CGG repeats in the DNA. In some examples, referring back to process 100 of FIG. 1, a genotype of the individual associated with the DNA size and abundance data may be determined at block 110 based on the one or more peaks identified at block 108. For example, if the DNA comprising the CGG-rich region includes the 5'-UTR of the FMR1 gene, the CGG repeat value associated with the peak identified at block 108 may be used to determine if the individual is a carrier for the FXS. In this example, if the peak identified at block 108 is centered at a CGG repeat value between 5-44, it may be indicative of a normal allele. If the CGG peak identified at block 108 is centered at a CGG repeat value between 45-54, it may be indicative of an intermediate allele. If the CGG peak identified at block 108 is centered at a CGG repeat value between 55-200, it may be indicative of a premutation allele. If the CGG peak identified at block 108 is centered at a CGG repeat value greater than 200, it may be indicative of a full mutation allele. In some examples, the gender, ethnicity, or the like, of the individual may be taken into consideration when determining the individual's genotype. For example, known distributions for a particular gender, ethnicity, or the like, may be used to modify the ranges of CGG repeat counts used to identify different genotypes.

Figure 4:
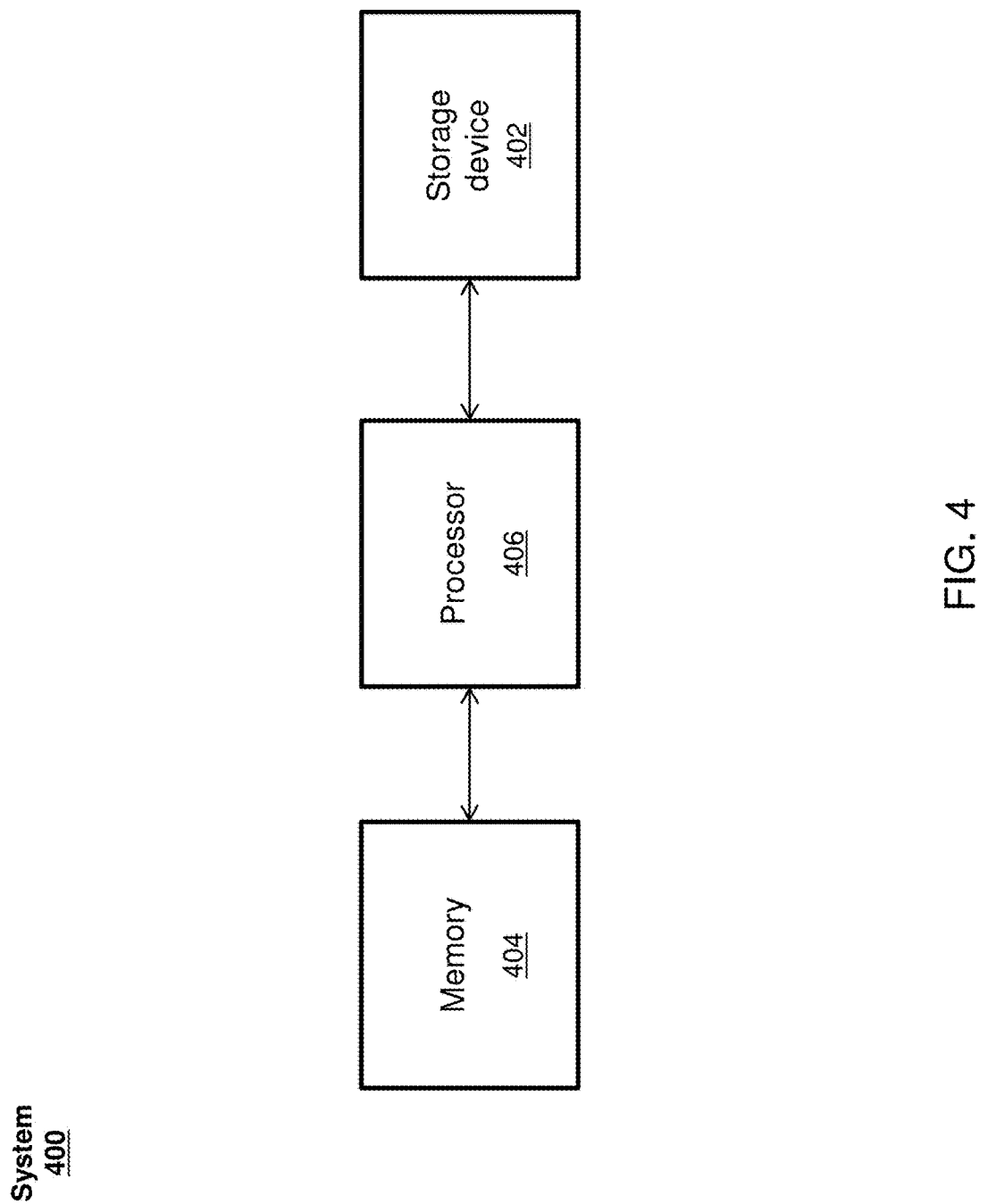
FIG. 4 illustrates an example computing system for determining a number of repeats of a nucleotide sequence in a gene according to various examples.

One or more of the functions relating to determining the number of CGG repeats can be performed by a system similar or identical to system 400 shown in FIG. 4. System 400 can include instructions stored in a non-transitory computer readable storage medium, such as memory 404 or storage device 402, and executed by processor 406. The instructions can also be stored and/or transported within any non-transitory computer readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer readable storage medium" can be any medium that can contain or store the program for use by or in connection with the instruction execution system, apparatus, or device. The non-transitory computer readable storage medium can include, but is not limited to, an electronic, magnetic, optical, electromagnetic, infrared, or semiconductor system, apparatus or device, a portable computer diskette (magnetic), a random access memory (RAM), a read-only memory (ROM), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The instructions can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

In some examples, system 400 can be configured to perform the blocks of process 100, described above. It is to be understood that the system is not limited to the components and configuration of FIG. 4, but can include other or additional components in multiple configurations according to various examples.

EXAMPLES

Example 1

Automated Population-Scale Screening for Fragile X Validation and Experience on Patient Samples CGG-repeat-primed PCR was run using AmplideX FMR1 PCR kits (Asuragen) and samples were analyzed on 3500/3500x1/3730x1 Genetic Analyzers (Applied Biosystems). We examined 76,421 samples with an indication of routine carrier screening (i.e., neither indicated family history nor infertility). 298 samples with apparent mosaicism (>2 peaks) were excluded from population analysis. 183 samples were from males; the other 76,238 were all from females.

We validated the calling algorithm on 60 externally-characterized samples from Coriell and further assessed its accuracy by manual review of its performance on the pool of clinical samples. Algorithm performance was measured by examining the amount of manual intervention in the course of results review by laboratory directors. Performance was measured in terms of peak calls.

The repetitive "stutter" signal in triplet-repeat-primed PCR defeats off-the-shelf peak calling software because it generates an individual peak at each CGG repeat. After resampling the CE data to be linear in bp-space (rather than CE scan number), a zero-phase FIR filter was used to remove the high-frequency stutter; peak calling using 1st/2nd derivative thresholding operated on this lowpass signal and precise peak positions are adjusted using a bandpass component incorporating stutter data.

On some samples, high (FAM) signal intensity impeded automatic detection of (ROX) ladder peaks necessary for sizing; crosstalk may add spurious peaks or remove true ones. We trained a prior distribution on expected locations of ladder peaks and matched observed peaks to the prior using dynamic programming to simultaneously assign peaks and minimize the squared-deviation in peak location:

$$\min\_dev(i, p) = \min\left[\min_{q=1}^{p-1}(\min\_dev(i-1, q) + \text{penalty}(i, p)),\right.$$
$$\left.\min_{q=1}^{p-1}(\min\_dev(i-2, q) + \text{penalty}(i, p)) + \text{MISSED\_PEAK\_PENALTY}\right]$$

$i$ indexes fragment sizes, $p$ indexes peaks

Figure 5:
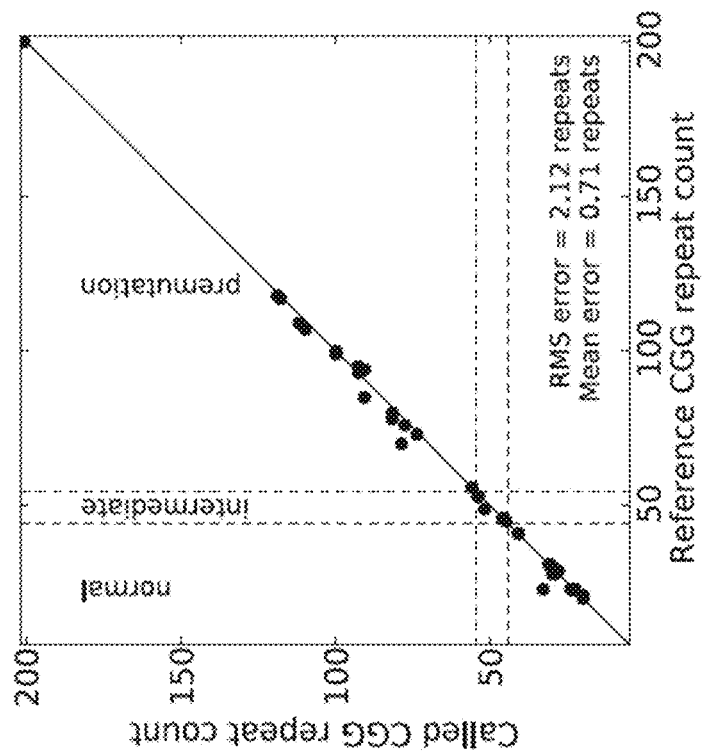
FIG. 5 shows validation and performance of 60 characterized Coriell samples.

As shown in FIG. 5, on 60 characterized Coriell samples, the automated caller achieved a mean error of 0.71 CGG repeats, an RMS error of 2.12 CGG repeats, and 100% accuracy of clinical classification. In validation against manual review on clinical samples, the caller showed 99.38% sensitivity with a 0.18% false positive rate.

On patient samples, the automated algorithm called 96,906 peaks with 204 false peaks and 702 missed peaks for a total sensitivity of 99.3%. On one CPU, the automated caller was 23× faster than manual calling. We found significant (P<0.01) population structure in allele size distributions. East Asians had a lower probability of intermediate or larger alleles and Middle Easterners had a higher probability. European and Ashkenazi Jewish allele sizes cluster together; South Asians, African-Americans, Middle Easterners, and Hispanics form a second cluster; and East and Southeast Asians form a third distinct cluster.

Our automated algorithm enables accurate high throughput population screening for Fragile X using CGG repeat-primed PCR. Automation enables a laboratory director to review a batch in 90 seconds rather than the half hour required for manual calling.

Figure 6:
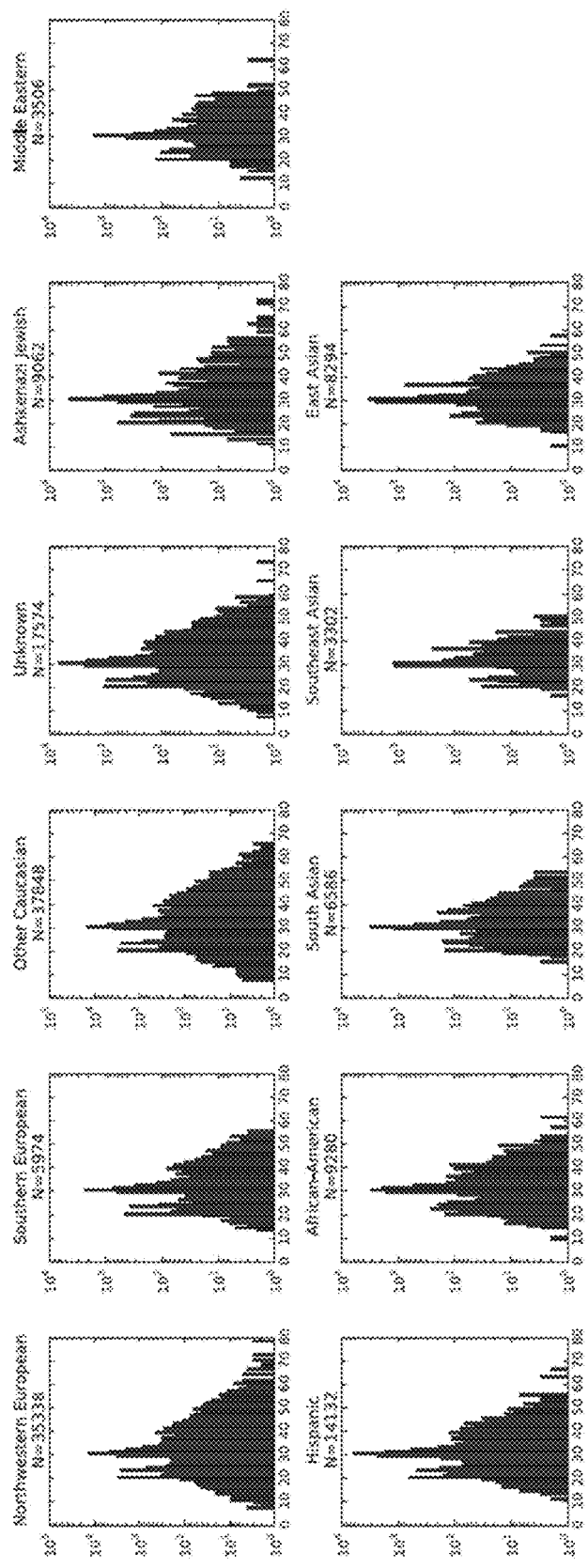
FIG. 6 shows log-scale histograms of allele size distribution by self-reported ethnicity.

FIG. 6 shows log-scale histograms of allele size distribution by self-reported ethnicity. N indicates the number of alleles. Only alleles <80 repeats are shown. In all populations, 30 is the most common repeat count. East and Southeast Asians have a smaller than usual peak before 30 repeats, and a larger peak at 37 repeats. Northwestern Europeans have an N=35,338, Southern Europeans have an N=5,974, other Caucasians have an N=37,848, unknowns have an N=17,574, Ashkenazi Jewish have an N=9,062, Middle Easterners have an N=3,506, Hispanics have an N=14,132, African-Americans have an N=9,280, South Asians have an N=6,586, Southeast Asians have an N=3,302, and East Asians have an N=8,294.

Figure 7:
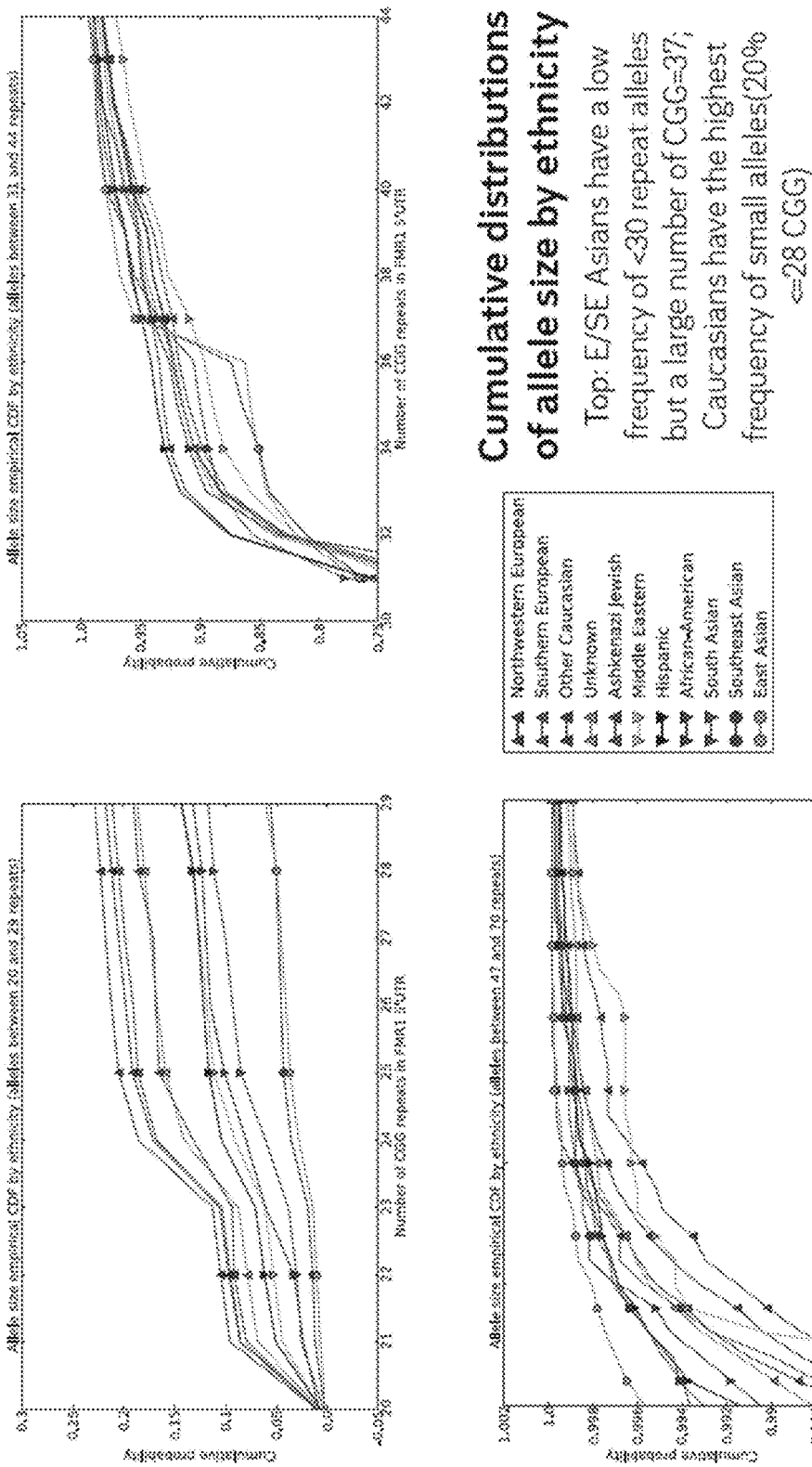
FIG. 7 shows cumulative distributions of allele size by ethnicity.

As shown in FIG. 7, we also present the first worldwide catalog of fragile X allele sizes. We find that East Asians tend to have shorter alleles and Middle Easterners longer ones, but that other groups appear to not be significantly differentiated for intermediate or larger alleles. Automated signal processing for triplet-repeat-primed PCR+CE-based testing for fragile X syndrome is efficient and reliable, allowing cost-effective population-scale carrier screening. FMR1 repeat lengths vary significantly by ethnicity: East and Southeast Asians have very low probabilities of both small (<30) and large (>45) alleles. East and Southeast Asians have a large number of CGG-37 alleles. Caucasians have the highest frequency of small alleles (20%<=28 CGG). Samples with reported Middle Eastern or Ashkenazi Jewish heritage showed a higher probability of alleles >45 repeats.

Figure 8:
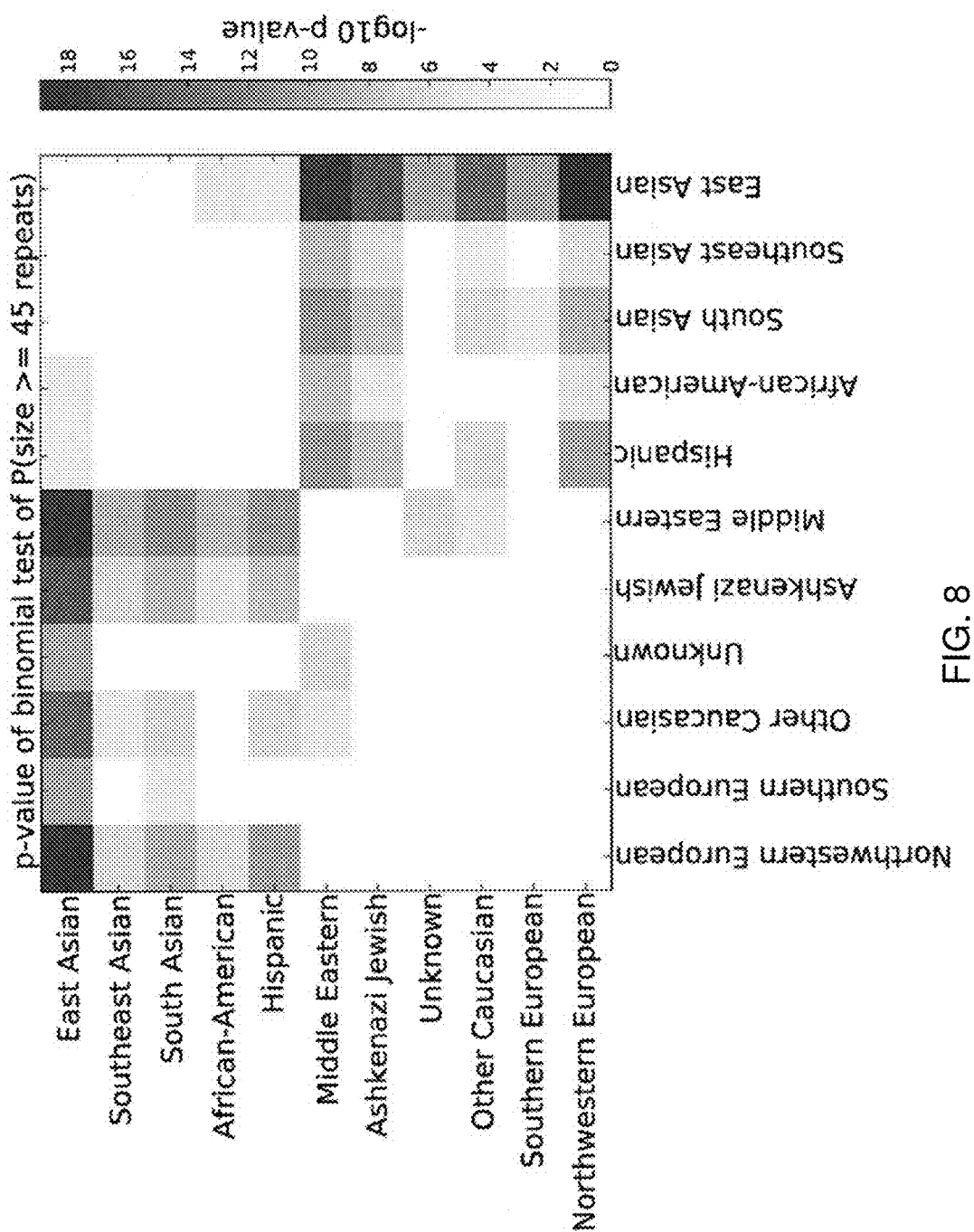
FIG. 8 shows distribution of large alleles.

FIG. 8 shows distribution of large alleles for East Asians, Southeast Asians, South Asians, African-Americans, Hispanics, Middle Easterners, Ashkenazi Jewish, unknown, other Caucasians, Southern Europeans, and Northwestern Europeans. $-\log 10$ of the p-value in a Bayesian binomial equality test to compare the probability of an individual having an intermediate or larger allele between ethnicities. Lightest color indicates "no significant difference" to P=0.01 (Bonferroni-corrected). Different Caucasian groups show no significant differences. East Asians significantly differ in probability of large alleles versus every other group except other Asians.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the appended claims.

What is claimed is:

1. A computer-implemented method for determining the number of CGG repeats in a DNA comprising a CGG-rich region, the method comprising:
   a) receiving, by one or more processors, DNA size and abundance data of DNA amplification products generated from the DNA comprising the CGG-rich region by using a primer set comprising a first primer recognizing the CGG-rich region and a second primer recognizing a region outside of the CGG-rich region;
   b) generating, by the one or more processors, a set of sample data by sampling the DNA size and abundance data at a sampling frequency;
   c) generating, by the one or more processors, a set of low-pass data by applying a lowpass filter to the set of sample data;
   d) generating, by the one or more processors, a set of band-pass data by applying a bandpass filter to the set of sample data;
   e) identifying, by the one or more processors, one or more peaks in the low-pass data;
   f) identifying, by the one or more processors, one or more peaks in the band-pass data; and
   g) identifying, by the one or more processors, a final peak representing a number of CGG repeats in the CGG-rich region based on the one or more peaks in the low-pass data and the one or more peaks in the band-pass data.

2. The computer-implemented method of claim 1, further comprising resolving the DNA amplification products to generate the DNA size and abundance data prior to step a).

3. The computer-implemented method of claim 2, wherein the resolving is carried out by capillary electrophoresis.

4. The computer-implemented method of claim 1, further comprising converting, by the one or more processors, the DNA size and abundance data from a time domain to a base-pair length domain prior to step b).

5. The computer-implemented method of claim 4, wherein a DNA ladder is used to convert the DNA size and abundance data from the time domain to the base-pair length domain.

6. The computer-implemented method of claim 1, wherein the sampling frequency is equal to four samples per base-pair.

7. The computer-implemented method of claim 1, wherein the band-pass filter has a low cutoff frequency of 2/13 multiplied by the sampling frequency and a high cutoff frequency of 2/11 multiplied by the sampling frequency.

8. The computer-implemented method of claim 1, wherein the low-pass filter has a cutoff frequency of $1.0*10^{-5}$ multiplied by the sampling frequency.

9. The computer-implemented method of claim 1, wherein the low-pass filter and the band-pass filter are zero-phase finite impulse response (FIR) filters implemented using a Hamming window.

10. The computer-implemented method of claim 1, wherein generating the set of sample data by sampling the DNA size and abundance data at the sampling frequency comprises:
    generating a linear interpolation of the DNA size and abundance data; and
    sampling the linear interpolation of the DNA size and abundance data at the sampling frequency.

11. The computer-implemented method of claim 1, wherein the set of sample data comprises a signal representing a combination of a CGG series of the CGG-rich region and a full-length amplicon of the DNA comprising the CGG-rich region, the set of band-pass data comprises a signal representing the CGG series of the CGG-rich region, and the set of low-pass data comprises a signal representing the full-length amplicon of the DNA comprising the CGG-rich region.

12. The computer-implemented method of claim 1, wherein identifying the final peak representing the number of CGG repeats in the DNA comprising the CGG-rich region comprises:
    removing peaks from the one or more peaks in the low-pass data having a width less than 4.5 base-pairs and a height less than a threshold value;
    removing peaks from the one or more peaks in the band-pass data having a width less than 4.5 base-pairs and a height less than the threshold value;
    removing peaks from the one or more peaks in the band-pass data having a height less than a height of an adjacent peak having a larger base-pair length;
    in response to a peak of the one or more peaks in the low-pass data having a height less than a height of a peak of the one or more peaks in the band-pass data that is within 3 base-pairs of the peak of the one or more peaks in the low-pass data, setting a center of the peak of the one or more peaks in the low-pass data to a center of the peak of the one or more peaks in the bandpass data, and setting a boundary of the peak of the one or more peaks in the low-pass data to a union of the peak of the one or more peaks in the low-pass data and the peak of the one or more peaks in the band-pass data;

merging peaks of the one or more peaks in the low-pass data and the one or more peaks in the band-pass data that have base-pair lengths greater than 165 base-pairs and that are within 30 base-pairs of each other; and merging peaks of the one or more peaks in the low-pass data and the one or more peaks in the band-pass data that are within 15 base-pairs and that are more than a factor of 2 different in height, wherein a remaining peak of the one or more peaks in the low-pass data is the final peak.

13. The computer-implemented method of claim 1, wherein the DNA comprising a CGG-rich region is a 5'-UTR of a fragile X mental retardation 1 gene (FMR1).

14. The computer-implemented method of claim 1, wherein the DNA comprising a CGG-rich region is a 5'-UTR of a fragile X mental retardation 2 gene (FMR2).

15. The computer-implemented method of claim 1, wherein the first primer comprises at least four CGG or CCG repeats.

16. The computer-implemented method of claim 1, wherein the primer set further comprises a third primer recognizing a region outside of the CGG-rich region that is on the opposite side as the region recognized by the second primer.

17. A computer-implemented method for determining a genotype associated with Fragile X syndrome in an individual, the method comprising:
a) performing DNA amplification reaction using a primer set comprising a first primer recognizing a CGG-rich region on a 5'UTR of a FMR1 gene and a second primer recognizing a region outside of a CGG-rich region on a 5'UTR of a FMR1 gene;
b) resolving the DNA amplification products to obtain DNA size and abundance data;
c) applying a low-pass filter and a band-pass filter to the DNA size and abundance data to identify a peak representing a number of CGG repeats in the CGG-rich region on the 5'UTR of the FMR1 gene; and
d) determining the genotype of the individual based on the identified peak.

18. The computer-implemented method of claim 17, wherein resolving is carried out by capillary electrophoresis.

19. The computer-implemented method of claim 17, further comprising converting, by the one or more processors, the DNA size and abundance data from a time domain to a base-pair length domain prior to step c).

20. The computer-implemented method of claim 19, wherein a DNA ladder is used to convert the DNA size and abundance data from the time domain to the base-pair length domain.

21. The computer-implemented method of claim 17, wherein the method further comprises sampling the DNA size and abundance data at a sampling frequency, and wherein applying the low-pass filter and the band-pass filter to the DNA size and abundance data comprises applying the low-pass filter and the band-pass filter to the sampled DNA size and abundance data.

22. The computer-implemented method of claim 21, wherein the sampling frequency is equal to four samples per base-pair.

23. The computer-implemented method of claim 21, wherein the band-pass filter has a low cutoff frequency of 2/13 multiplied by the sampling frequency and a high cutoff frequency of 2/11 multiplied by the sampling frequency.

24. The computer-implemented method of claim 21, wherein the low-pass filter has a cutoff frequency of $1.0*10^{-5}$ multiplied by the sampling frequency.

25. The computer-implemented method of claim 21, wherein sampling the DNA size and abundance data at the sampling frequency comprises:
generating a linear interpolation of the DNA size and abundance data; and
sampling the linear interpolation of the DNA size and abundance data at the sampling frequency.

26. The computer-implemented method of claim 17, wherein the low-pass filter and the band-pass filter are zero-phase finite impulse response (FIR) filters implemented using a Hamming window.

27. The computer-implemented method of claim 17, wherein the DNA size and abundance data comprises a signal representing a combination of a CGG series of the FMR1 gene and a full-length amplicon of the 5' UTR of the FMR1 gene, the set of band-pass data comprises a signal representing the CGG series of the FMR1 gene, and the set of low-pass data comprises a signal representing a full-length amplicon of the 5' UTR of the FMR1 gene.

28. The computer-implemented method of claim 17, wherein identifying the peak representing the number of CGG repeats in the CGG-rich region on the 5'UTR of the FMR 1 gene comprises:
removing peaks from the one or more peaks in an output of the low-pass filter having a width less than 4.5 base-pairs and a height less than a threshold value;
removing peaks from the one or more peaks in an output of the band-pass filter data having a width less than 4.5 base-pairs and a height less than the threshold value;
removing peaks from the one or more peaks in the output of the band-pass filter having a height less than a height of an adjacent peak having a larger base-pair length;
in response to a peak of the one or more peaks in the output of the low-pass filter having a height less than a height of a peak of the one or more peaks in the output of the band-pass filter that is within 3 base-pairs of the peak of the one or more peaks in the output of the lowpass filter, setting a center of the peak of the one or more peaks in the output of the low-pass filter to a center of the peak of the one or more peaks in the output of the band-pass filter, and setting a boundary of the peak of the one or more peaks in the output of the low-pass filter to a union of the peak of the one or more peaks in the output of the low-pass filter and the peak of the one or more peaks in the output of the band-pass filter;
merging peaks of the one or more peaks in the output of the low-pass filter and the one or more peaks in the output of the band-pass filter that have base-pair lengths greater than 165 base-pairs and that are within 30 base-pairs of each other; and
merging peaks of the one or more peaks in the output of the low-pass filter and the one or more peaks in the output of the band-pass filter that are within 15 base-pairs and that are more than a factor of 2 different in height, wherein a remaining peak of the one or more peaks in the output of the low-pass filter is the final peak.

29. The computer-implemented method of claim 17, further comprising determining whether the individual is a carrier for fragile X syndrome based on the genotype of the individual, wherein a number of CGG repeats in the CGG-rich region on the 5'UTR of the FMR1 gene between 5-44 repeats is indicative of a normal allele, a number of CGG repeats in the CGG-rich region on the 5'UTR of the FMR1 gene between 45-54 repeats is indicative of an intermediate allele, a number of CGG repeats in the CGG-rich region on the 5'UTR of the FMR1 gene between 55-200 repeats is indicative of a premutation allele, and wherein a number of CGG repeats in the CGG-rich region on the 5'UTR of the FMR1 gene greater than 200 repeats is indicative of a full mutation allele.

30. A computer-implemented method for determining the number of nucleic acid repeats in a DNA comprising a nucleic acid repeat region, the method comprising:
  a) receiving, by one or more processors, DNA size and abundance data of DNA amplification products generated from the DNA comprising the nucleic acid repeat region by using a primer set comprising a first primer recognizing the nucleic acid repeat region and a second primer recognizing a region outside of the nucleic acid repeat region;
  b) generating, by the one or more processors, a set of sample data by sampling the DNA size and abundance data at a sampling frequency;
  c) generating, by the one or more processors, a set of low-pass data by applying a lowpass filter to the set of sample data;
  d) generating, by the one or more processors, a set of band-pass data by applying a bandpass filter to the set of sample data;
  e) identifying, by the one or more processors, one or more peaks in the low-pass data;
  f) identifying, by the one or more processors, one or more peaks in the band-pass data; and
  g) identifying, by the one or more processors, a final peak representing a number of nucleic acid repeats in the nucleic acid repeat region based on the one or more peaks in the lowpass data and the one or more peaks in the band-pass data.

31. The computer-implemented method of claim 30, wherein the set of sample data comprises a series of periodic peaks corresponding to successively longer CGG repeat sequences.

32. The computer-implemented method of claim 30, wherein identifying the final peak comprises centering at least one of the one or more peaks in the low-pass data to the center of one of the one or more peaks in the band-pass data.

* * * * *